(12) United States Patent　　(10) Patent No.: US 8,999,726 B2
Chang-Yen et al.　　(45) Date of Patent: Apr. 7, 2015

(54) MICROFLUIDIC INTERFACE FOR HIGHLY PARALLEL ADDRESSING OF SENSING ARRAYS

(71) Applicant: University of Utah Research Foundation, Salt Lake City, UT (US)

(72) Inventors: David A. Chang-Yen, West Jordan, UT (US); Sriram Natarajan, Salt Lake City, UT (US); Josh Eckman, West Bountiful, UT (US); Bruce K. Gale, Salt Lake City, UT (US); David Myszka, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/776,601

(22) Filed: Feb. 25, 2013

(65) Prior Publication Data

US 2014/0235510 A1　　Aug. 21, 2014

Related U.S. Application Data

(62) Division of application No. 11/241,060, filed on Sep. 30, 2005, now Pat. No. 8,383,059.

(51) Int. Cl.
　　*G01N 1/10*　　(2006.01)
　　*G01N 33/553*　　(2006.01)
　　(Continued)

(52) U.S. Cl.
　　CPC ........... *G01N 33/553* (2013.01); *B01J 19/0046* (2013.01); *B01L 3/502715* (2013.01); *G01N 35/1074* (2013.01); *C12N 15/1093* (2013.01); *B01L 3/0293* (2013.01); *B01L 3/5025* (2013.01); *B01L 3/50273* (2013.01); *B01L 2200/021* (2013.01); *B01L 2300/0636* (2013.01); *B01L 2300/0819* (2013.01); *B01L 2300/0822* (2013.01); *B01L 2300/0877* (2013.01);
　　(Continued)

(58) Field of Classification Search
　　USPC ............ 436/43, 180; 422/408, 501–505, 509, 422/518–51; 506/27, 30, 32–40
　　See application file for complete search history.

(56) References Cited

U.S. PATENT DOCUMENTS 5,811,306 A * 9/1998 Komatsu .................... 436/54
6,090,251 A 7/2000 Sundberg et al.
(Continued)

FOREIGN PATENT DOCUMENTS

JP　　H 11281534　　10/1999

*Primary Examiner* — Brian R Gordon

(57) ABSTRACT

Disclosed is a spotter device and methods for the formation of microassays, biochips, biosensors, and cell cultures. The spotter may be used to deposit highly concentrated spots of protein or other materials on a microarray slide, wafer, or other surface. It may also be used to perform various chemistry steps on the same spots. The spotter increases the surface density of substances at each spot by directing a flow the desired substance (or a solution thereof) over the spot area until surface saturation is accomplished. The spotter may be loaded by well plate handling equipment. The spotter uses wells, microfluidic conduits, and orifices to deposit proteins, other biomolecules, or chemicals on a spot on, a separate surface. Each orifice is connected to two wells via microconduits. When the spotter contacts a surface, a seal is formed between the orifices and the surface. The same or different substances may be flowed across each orifice. Any number of orifices may be incorporated into a spotter. The spotter is particularly useful for depositing proteins in high concentrations on a surface, since the spotter may be placed on a surface for an extended period of time.

12 Claims, 12 Drawing Sheets

(51) Int. Cl.
  *B01J 19/00* (2006.01)
  *B01L 3/00* (2006.01)
  *G01N 35/10* (2006.01)
  *C12N 15/10* (2006.01)
  *B01L 3/02* (2006.01)
  *G01N 35/00* (2006.01)

(52) U.S. Cl.
  CPC ............ B01L2400/0487 (2013.01); G01N 2035/00158 (2013.01); G01N 2035/1039 (2013.01)

(56) References Cited

U.S. PATENT DOCUMENTS

| | | | |
|---|---|---|---|
| 6,110,426 A | 8/2000 | Shalon et al. | |
| 6,274,091 B1 | 8/2001 | Mohan et al. | |
| 6,365,349 B1 | 4/2002 | Moynihan et al. | |
| 6,391,625 B1 | 5/2002 | Park et al. | |
| 6,461,812 B2 * | 10/2002 | Barth et al. | 435/6.1 |
| 6,485,690 B1 * | 11/2002 | Pfost et al. | 422/552 |
| 6,503,715 B1 | 1/2003 | Gold et al. | |
| 6,594,432 B2 | 7/2003 | Chen et al. | |
| 6,596,237 B1 | 7/2003 | Borrelli et al. | |
| 6,623,696 B1 | 9/2003 | Kim et al. | |
| 6,656,740 B1 * | 12/2003 | Caren et al. | 506/16 |
| 6,699,719 B2 | 3/2004 | Yamazaki et al. | |
| 6,733,968 B2 | 5/2004 | Yamamoto et al. | |
| 6,762,061 B1 | 7/2004 | Borrelli et al. | |
| 6,833,112 B2 | 12/2004 | Hoummady | |
| 6,872,359 B2 | 3/2005 | Caren et al. | |
| 6,884,626 B1 * | 4/2005 | Borrelli et al. | 436/180 |
| 7,025,935 B2 | 4/2006 | Jones et al. | |
| 7,402,286 B2 * | 7/2008 | Pinkel et al. | 422/504 |
| 7,955,865 B2 * | 6/2011 | Marziali et al. | 436/180 |
| 8,173,068 B2 * | 5/2012 | Loeffler et al. | 422/68.1 |
| 8,357,339 B2 * | 1/2013 | Peltier | 422/534 |
| 2001/0020588 A1 | 9/2001 | Adourian et al. | |
| 2001/0053337 A1 * | 12/2001 | Doktycz et al. | 422/100 |
| 2002/0121529 A1 * | 9/2002 | Hoummady | 222/113 |
| 2002/0164824 A1 | 11/2002 | Xiao et al. | |
| 2003/0003025 A1 * | 1/2003 | MacAulay et al. | 422/100 |
| 2003/0003027 A1 | 1/2003 | Albert et al. | |
| 2003/0068253 A1 | 4/2003 | Bass et al. | |
| 2003/0099577 A1 | 5/2003 | Renaud et al. | |
| 2003/0124734 A1 | 7/2003 | Dannoux | |
| 2003/0228241 A1 * | 12/2003 | Legge | 422/100 |
| 2004/0014102 A1 | 1/2004 | Chen et al. | |
| 2004/0109793 A1 | 6/2004 | McNeely et al. | |
| 2005/0047962 A1 | 3/2005 | Laurell et al. | |
| 2005/0249641 A1 | 11/2005 | Blankenstein et al. | |
| 2005/0266582 A1 | 12/2005 | Modlin et al. | |
| 2006/0040398 A1 | 2/2006 | Schulz et al. | |
| 2006/0233673 A1 | 10/2006 | Beard et al. | |
| 2006/0286001 A1 | 12/2006 | Sundberg et al. | |
| 2010/0075860 A1 * | 3/2010 | Myszka et al. | 506/7 |
| 2010/0248994 A1 * | 9/2010 | Gale et al. | 506/32 |
| 2014/0171342 A1 * | 6/2014 | Gale et al. | 506/32 |

* cited by examiner

MICROFLUIDIC INTERFACE FOR HIGHLY PARALLEL ADDRESSING OF SENSING ARRAYS

This application is a divisional of U.S. patent application Ser. No. 11/241,060, filed on Sep. 30, 2005, which is incorporated herein by reference.

STATEMENT REGARDING FEDERALLY SPONSORED RESEARCH OR DEVELOPMENT

Work described herein was supported National Science Foundation Grant #DGE 9987616. The United States Government may have certain rights in the invention.

TECHNICAL FIELD

The present invention relates generally to biotechnology, more specifically to building microassays, biochips, and biosensors. In particular, the present invention encompasses a device with micro fluidic channels for the deposition of a substance on a substrate.

BACKGROUND

In recent years, a large number of biological/chemical analysis techniques have been demonstrated using microscale systems and have been implemented using micromachining technology. The rationale for using microscale technologies in analytical instrumentation includes reduction in instrument size and cost, reduction in sample and reagent volume, reduction in analysis time, increase in analysis throughput, and the possibility of integration of sample preparation and analysis functions.

Currently, high spot density arrays are produced using robotic spotter systems, such as the GENETIX QARRAY(R). One of the current techniques uses spotting "pens" which collect the material to be deposited on a needle and then "spots" the material on to a substrate. See, e.g., U.S. Pat. No. 6,733,968 to Yamamoto et al., ("'968 patent") entitled "Microarray, Method for Producing the Same, and Method for Correcting Inter-Pin Spotting Amount Error of the Same." The '968 patent notes that when multiple "pens" are used to create an array, not all of the "pens" are microscopically the same size, and therefore each "pen" blots a different amount of solution. The patent discloses a method for determining what the errors are for a given set of "pens" so the errors can be mathematically accounted for.

U.S. Pat. No. 6,365,349 to Moynihan et al., entitled "Apparatus and Methods for Arraying Solution onto a Solid Support," discloses the use of a spring probe to administer samples onto a substrate.

Similar to the use of "pens" is the use of capillaries. See e.g., U.S. Patent Application 20040014102, Chen et al., entitled "High Density Parallel Printing of Microarrays." The application discloses the use of capillaries to spot samples onto a microarray. U.S. Pat. No. 6,594,432 to Chen et al. ("'432 patent"), entitled "Microarray Fabrication Techniques and Apparatus," also discloses the use of capillaries, such as silica tubes, to spot probes onto a substrate. In the '432 patent, one end of the capillaries may be attached to a reservoir; however there is no return path for the substance that is spotted and therefore no way to flow a substance over a substrate to increase the spot deposition density. The capillary action of the '432 patent is therefore similar to that done with pens. For an additional example see, U.S. Pat. No. 6,110,426 to Shalon et al., entitled "Methods for Fabricating Microarrays of Biological Samples," which discloses a method for tapping a meniscus at the end of a capillary tube to deliver a specified amount of sample material onto a substrate.

While prior art systems are capable of producing multiple spots of a controlled size, if the desired molecule for deposition is present in very low concentration, the total number of desired molecules that can be deposited on the surface is severely limited for a single spot. The concentration of material in the spots is limited by the concentration of the original material and the spot size. The Perkin-Elmer BIOCHIP ARRAYER(R) uses "ink jet printing" technology, but that method has the same concentration limitation as the "pens."

Other systems have been developed which use microfluidic channels on a substrate to pattern genes, proteins, nucleic acids, such as RNA, DNA, oligonucleic acids, or other arrays. For an example of such a system see, U.S. Pat. No. 6,503,715 to Gold et al., entitled "Nucleic Acid Ligand Diagnostic Biochip." Biochip fabrication methods have been developed that attempt to stir individual microassay spots; however, such systems often require mechanical manipulation of the biochip. See e.g., U.S. Pat. No. 6,623,696 to Kim et al., entitled "Biochip, Apparatus for Detecting Biomaterials Using the Same, and Method Therefor," which discloses spinning a biochip in order to accelerate reaction time. A need exists to simplify the process of developing biochips and biosensors and for providing more control over individual spots on the biochips and biosensors.

Ideally, a flow deposition system could produce a high surface density if the substrate surface were tailored to bond only to the desired molecules, allowing the unwanted bulk material to be washed away. However, flow deposition systems generally are incapable of producing spot arrays, let alone individually addressed arrays. See, e.g., Japan Patent Application 10084639, Tomoko et al., entitled "Method and Apparatus for Adding Sample." That application discloses a method wherein a biochip is rotated and centrifugal forces are used to uniformly spread a sample over the entire surface of the biochip. Similarly, U.S. Pat. No. 6,391,625 to Park et al., entitled "Biochip and Method for Patterning and Measuring Biomaterial of the Same," discloses a method for making biochips via irradiating portions of the substrate with a laser and then spin coating probe molecules onto the substrate.

Additionally, current technology is unable to sequentially chemically process individual spots, or to perform layer-by-layer self-assembly (LBL) to build up the spot concentration. What is needed is a way to take molecules in a solution and adhere a high-concentration of those molecules on a substrate. This would be particularly advantageous in studying protein function.

Additionally, microarray-type structures are used in forming biosensors and the same problems associated with biochips apply to biosensors. See e.g., U.S. Pat. No. 6,699,719 to Yamazaki et al., entitled "Biosensor Arrays and Methods," which discloses using microarray forming techniques in the formation of a biosensor. A need exists to simplify the creation the biosensors.

A need exists to decrease the cost and time involved in processing microarrays as well. Attempts have been made to address that need, see e.g., U.S. Patent Application 2003/0068253 A1, Bass et al., entitled "Automation-Optimized Microarray Package," which discloses a method for automating microarray processing via a linear strip of microarrays that is processed in an assembly line fashion. Lab-on-a-chip micro fluidic devices have included sample wells directly above microfluidic channels; however, a need exists to simplify the cost and time of loading those sample wells.

SUMMARY OF THE INVENTION

The present invention includes a method and apparatus capable of patterning the surface of microarrays with a high-concentration of individually addressed spots. The present invention includes a method of manipulating the inventive apparatus by well plate handling equipment. The methods and apparatus of the present invention may be used to increase the surface density at a spot by directing a flow of a substance over the spot area until a desired surface deposition density is accomplished.

One embodiment of the invention is a spotter apparatus for depositing a substance on a surface in an ordered array. The spotter including a support surface; a plurality of wells formed in the support surface in substantially the same spacing and format as a well plate and each of the plurality of wells having a capacity to hold a quantity of fluid; a plurality of microconduits with holes in the sidewall of each of the plurality of microconduits; the plurality of microconduits operably connected to the plurality of wells; and the plurality of microconduit holes arranged along a different surface of the spotter.

Another embodiment of the invention is a method of depositing at least one substance on a surface including loading a multiplicity of storage zones of a micro spotter, via sample handling equipment, with the at least one substance; placing a face of the microspotter in proximity to the surface sufficient to form a seal between the microspotter face and the surface, wherein the microspotter face includes orifices fluidically connected to the multiplicity of storage zones; flowing the at least one substance from the loaded multiplicity of storage zones to the orifices and into contact with the surface sufficient to deposit at least a portion of the at least one substance on the surface; and flowing the remaining undeposited at least one substance to a previously unloaded multiplicity of storage zones.

Another embodiment of the invention is a method of loading a spotter for depositing a substance on a surface including positioning a spotter via a positioning means; and loading the substance into a plurality of wells of the spotter via a loading means, the spotter comprising a means for holding a plurality of wells, the wells adapted to hold a quantity of fluid and having a predetermined spacing between adjacent wells, a plurality of microconduit means connected to each well, and aperture means within said plurality of microconduits, the aperture means arranged operable to form a seal with the surface.

DETAILED DESCRIPTION OF THE INVENTION

Figure 1:
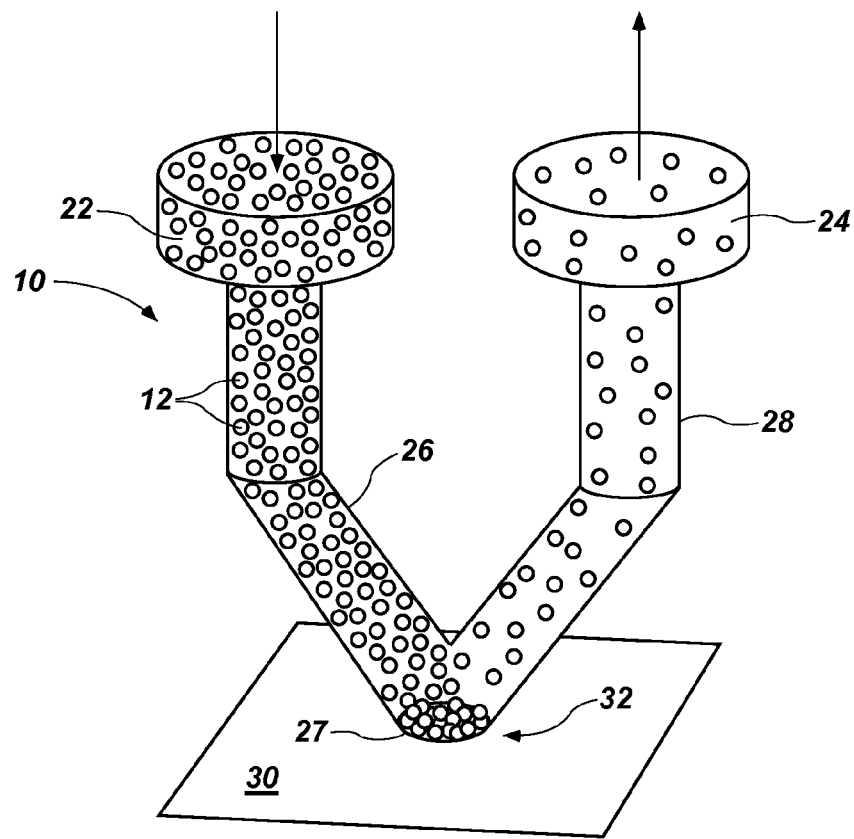
FIG. 1 idealizes deposition of a substance on a surface.

Disclosed is a spotter capable of patterning the surface of microarrays with a high-concentration of individually addressed spots and methods of using and fabricating the spotter. The spotter is also easily manipulated by well plate handling equipment. The invention includes microconduits of that may be used to increase the surface density at each spot by directing a flow of a substance, such as probe and/or target molecules, over the spot area until a desired surface deposition density is accomplished.

As used herein, the term "substance" includes probes, samples, target compounds, cells, nutrients, and/or carriers. Examples of "probes" include: proteins; nucleic acids, including deoxyribonucleic acids (DNA) and ribonucleic acids (RNA); cells; peptides; lectins; modified polysaccharides; synthetic composite macromolecules, functionalized nanostructures; synthetic polymers; modified/blocked nucleotides/nucleosides; synthetic oligonucleotides; modified/blocked amino acids; fluorophores; chromophores; ligands; receptors; chelators; haptens; drug compounds; antibodies; sugars; lipids; liposomes; cells; viruses; any nano- or microscale objects; and any chemical compounds that have associated substances which binds, associates, or interacts with other probe materials. Target compounds are typically flowed over probes or combinations of probes already bound to a substrate. "Carrier" refers to a vehicle for transporting probes, cells, target compounds, or nutrients. "Carriers" includes solvents (e.g., any aqueous or non-aqueous fluid and/or gel), and may have particles suspended therein.

"Deposit" as the term is used herein includes adsorbing a substance onto a surface, adsorbing a different substance onto a surface, chemically reacting a substance on a surface, performing various chemistry steps upon the spot, or removing a portion of a substance at the spot, such as an amino acid sequence from a protein.

First, will be described some of the embodiments of the spotter. Next, uses of the spotter will be discussed followed by experimental data generated by some of the embodiment of the spotter. 1.0 Structure In one embodiment, the spotter includes a support surface; a plurality of wells formed in the support surface in substantially the same spacing and format as a well plate and each of the plurality of wells having a capacity to hold a quantity of fluid; a plurality of microconduits with holes in the sidewall of each of the plurality of microconduits; the plurality of microconduits operably connected to the plurality of wells; and the plurality of microconduit holes arranged along a different surface of the spotter.

Another embodiment of the spotter is a means for holding a plurality of wells, the wells adapted to hold a quantity of fluid and having a predetermined spacing between adjacent wells, a plurality of microconduit means connected to each well, and aperture means within said plurality of microconduits, the aperture means arranged operable to form a seal with a surface.

PCT Patent Application, Application No. PCT/US05/23895, designating the United States of America, Spotting Device And Method For High Concentration Spot Deposition On Microarrays And Other Microscale Devices, is incorporated herein by reference in its entirety.

FIG. 1 is an idealized non-proportional illustration of the increasing deposition concentration possible with the invention. Spotter 10 has a well 22 and a well 24. Well 22 is connected to microconduit 26 which in turn is connected to microconduit 28. Well 24 is connected to microconduit 28. At the junction of microconduits 26 and 28 is orifice 27. When spotter 10 is sufficiently pressed against a surface 30, the orifice 27 forms a seal with the surface 30. The area on surface 30 bounded by the orifice is spot 32. Well 22 may be loaded with substance 12. As positive pressure is applied to well 22, substance 12 flows from well 22 to well 24. As substance 12 is flowing over spot 32, a portion of the substance deposits on spot 32. This allows spot 32 to increase in deposition density. Microconduits 26 and 28 may be viewed as separate microconduits with a junction at orifice 27. However, microconduits 26 and 28 may also be viewed as a single microconduit extending from well 22 to well 24 with a hole in the sidewall of the microconduit forming orifice 27.

Microconduits as used herein refers to channels, microchannels, canals, microcanals, microtubules, tubules and/or tubes. For example, microconduits 26 and 28 of FIG. 1 may be channels in a block or tubes without a supporting block structure. Microconduits may refer to single fluid pathways connecting an orifice to two or more wells. Microconduits also refers to a single pathway that connects two wells and has an orifice, hole, or aperture in the side thereof.

Orifice as used herein refers to the openings in the spotter where a substance may be delivered by the spotter to a substrate. "Orifice" includes the terms "microconduit holes," "apertures," and "spotting holes."

The spotter in FIG. 1 only illustrated 2 wells; however, a spotter may have any number of wells. It can be beneficial to have the wells in the same number and orientation as a well plate, the function and structure thereof to be described hereinafter. This allows well plate handling devices and technology to be used in loading and unloading the spotter as will be discussed in more detail below. There are a variety of well plate arrays, for example, 8, 16, 96, 384, or 1536 well well plates. Well plates may also be referred to as micro titer plates. A spotter may include any of the above well-plate arrays including larger or different well plate designs that come about in the future. The surface of the spotter where the wells are formed is referred to herein as the top surface or support surface of the spotter. However, that is not to be construed as limiting the orientations in which the spotter may be used. For example, the top surface of the particular 16 well embodiment shown in FIG. 6 may be horizontal and facing up, it may be vertically orientated, horizontal and facing down, or any variation in between. Additionally, even though surface wherein the wells are formed is referred to as the "top" any number of other structures, such as pumping manifolds or glass plates, may be placed over the top of the spotter.

Figure 14:
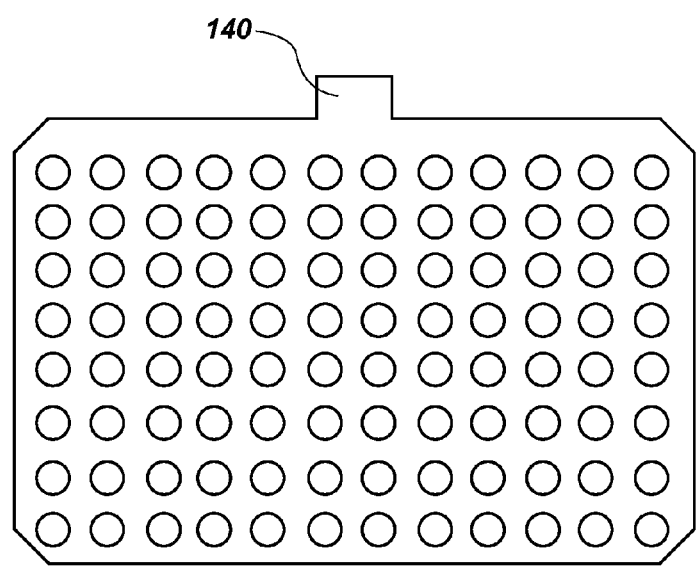
FIG. 14 is an embodiment of a 48-orifice spotter.
Figure 15:
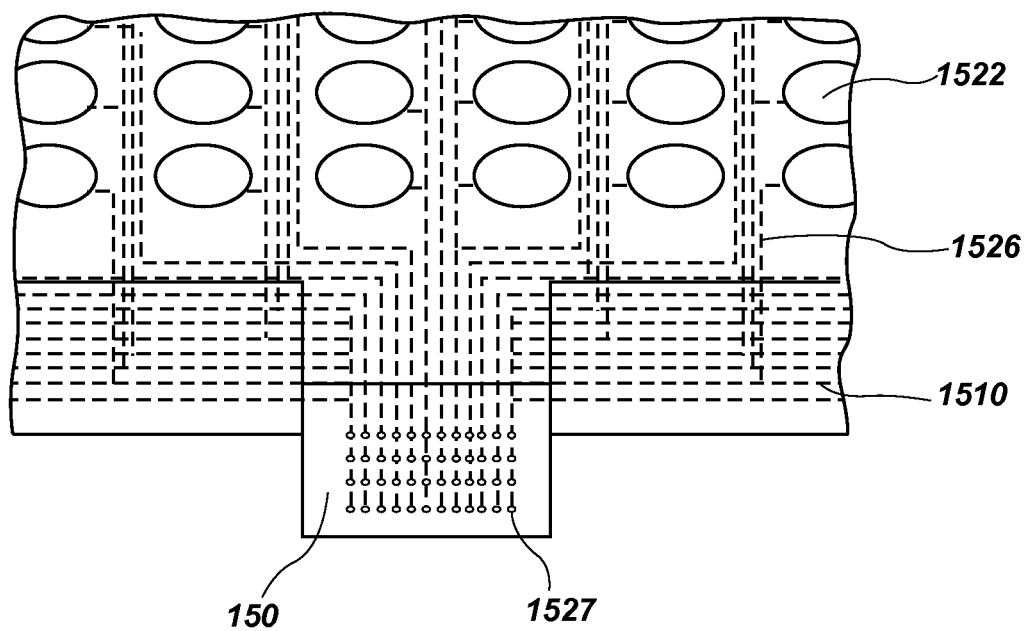
FIG. 15 is a close up of the spotter face of the embodiment shown in FIG. 14.

The orifices in the microconduits are preferably arranged along a single surface of the spotter. The surface where the orifices are arranged may also be referred to as the spotter face. FIGS. 14 and 15 illustrate an embodiment of a 96 well spotter where the orifices are orientated along a side surface of the spotter. In the embodiment shown in FIGS. 14 and 15, the spotter face 150 is projected away from the side of the spotter 1510 via a projection neck 140. FIG. 15 also illustrates orifices 1527, wells 1522, and microconduits 1526. However, the spotter face 150 may be integrated into the side of the spotter 1510 without a projection neck 140 projecting the spotter face 150 away from the spotter 1510. The spotter face 150 may also be integrated into the bottom surface of the spotter 1510.

The spotter face is adapted to form a seal with a desired surface. Often the surface will be relatively smooth such a microslide or wafer. However, the spotter face and the orifices may be configured to mate with any surface. For example, if a surface has existing wells or canals, the spotter face and orifices can be modified so that the orifices are able to form a seal with the uneven surface.

Generally, the spotter orifices will be arranged in a 2-D array. The array can be in a chess board or honeycomb pattern. However, there may be situations where a different orifice pattern such as a random pattern may be desired. Any number of orifice patterns can be built into the spotter face.

The spotter may include any number of orifices. In one variation of the embodiments, there are two wells for each orifice. Therefore, a spotter with 1536 wells would have 768 orifices. A spotter with 384 wells would have 192 orifices. A spotter with 96 wells would have 48 orifices. A spotter with 16 wells would have 8 orifices and so on. This variation allows a pumping manifold to be placed over half of the wells and substances placed in the other half of the wells. A pump is connected to the pump manifold, and the pump then delivers alternating positive pressure and vacuum pressure. This cycles the substances back and forth between the wells via the microconduits.

As used herein, the term "pump" includes devices that can deliver positive pressure, alternating positive pressure and vacuum pressure, or just vacuum pressure. Gravity flow may be used as the pump as well. Similarly, "pumping manifold" refers to any device for interfacing between the spotter wells and the pump, regardless of whether positive pressure or vacuum pressure is being delivered.

Figure 6:
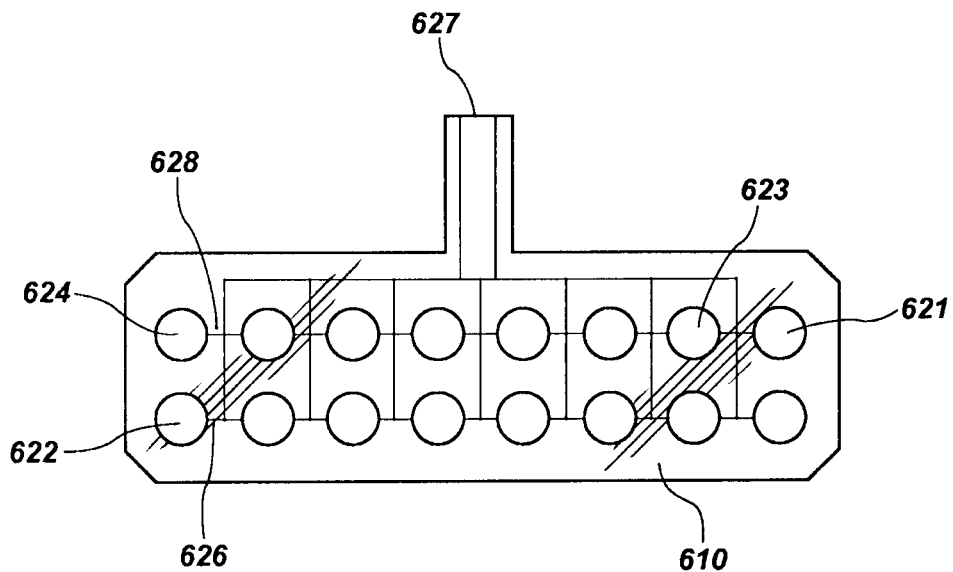
FIG. 6 is one embodiment of an eight-orifice spotter.
Figure 7:
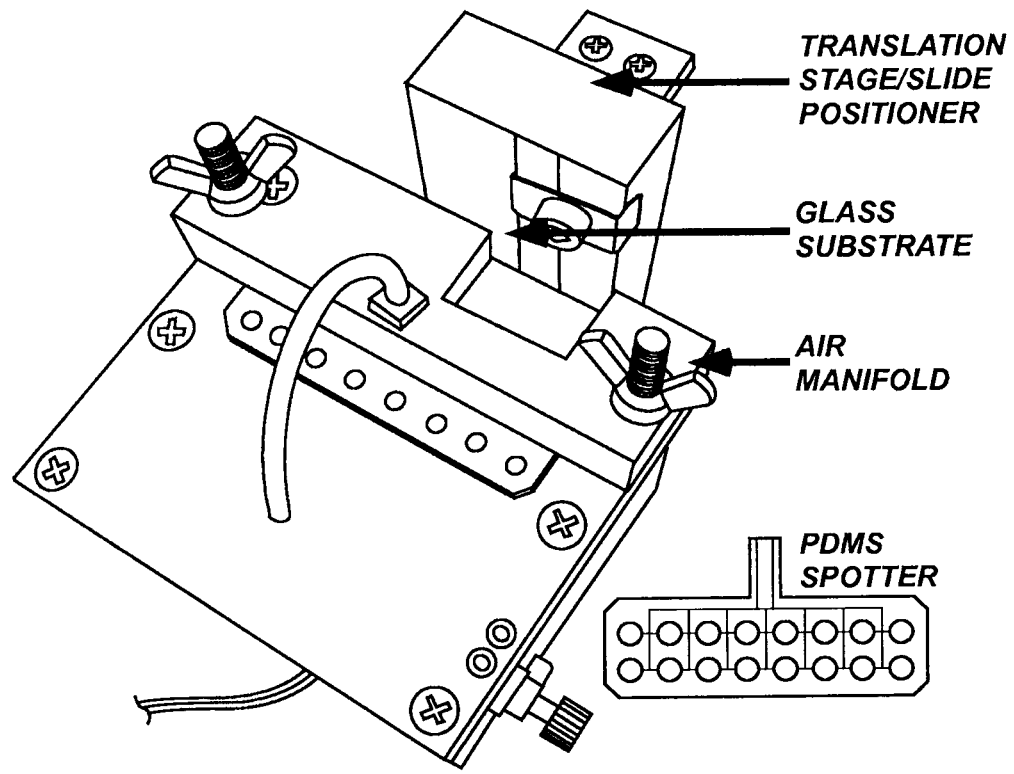
FIG. 7 is one embodiment of an automated use of the spotter of FIG. 6.

For example, in the 16 well embodiment shown in FIGS. 6 and 7, the front row wells (referring to the "front" as the row closest to the spotter face) serve to interface with the pumping manifold and the back row is loaded with the substances. The wells that interface with the pumping manifold will be referred to as "pump wells." The wells that are loaded with substances will be referred to as "sample wells." In this example, there would be eight separate fluid pathways connecting eight pump wells and eight samples wells to eight orifices. Each column of wells in this particular embodiment contains a pump well and a sample well. For example, well 622 is connected to microconduit 626. Microconduit 626 junctions with microconduit 628 at orifice 627. Microconduit 628 connects to well 624. As vacuum pressure is first applied to the front row pump wells, substances are drawn through microconduits unique to that well, to the orifice where the substance contacts a surface (such as an assay microslide), the substance is then drawn through a second unique microconduit which leads to the pump wells. The process is then reversed by applying positive pressure to the pumping manifold. Pushing the substances back through the microconduits and to the sample wells. Thus, resulting in oscillating eight potentially different substances over eight spots on the surface to which the spotter orifices are sealed. This also results in preserving the substances that do not deposit onto the surface spots. Of course, it may be desirable to not oscillate the substance over the spots, and instead to preserve the substance in the pump wells after the substance has come in contact with the surface and any probes on the surface.

Of course, the pumping manifold may also be placed over the sample wells. That would merely require first applying positive pressure and then applying vacuum pressure.

Another variation of the embodiments is where only a few of the wells are pump wells. Well plates are generally organized in 2-D arrays; and the wells of the spotter embodiments shown in the FIGS. are also in 2-D arrays. A single row or column of the well array could be pump wells, and the remaining wells could be for sample wells. That would increase the number of orifices that would be available for spotting.

For example, the particular 16 well spotter shown in FIGS. 6 and 7, spotter 610, could dedicate wells 622 and 624 as pump wells. Therefore, the pumping manifold, instead of interfacing with the front row of wells, would interface only with wells 622 and 624. That would allow for 14 orifices rather eight. Now, instead of each column containing a pump well and a sample well, each row would contain one pump well and seven sample wells. Each of the seven sample wells would each uniquely connect to an orifice. For example, well 621 would connect to a first unique orifice and well 623 would connect to a second unique orifice. Separate microconduits would then connect the first and second unique orifices to well 624. The same would be true of the other 5 wells in the front row of spotter 610. Therefore, well 624 could serve as the pump well and the other seven wells including wells 621 and 623 would serve as the sample wells. The same setup would exist for the back row of spotter 610 and well 622. Therefore, there would be 14 sample wells, 14 orifices, and 2 pump wells. It may be desirable in this embodiment to not oscillate the substance back and forth between the wells, particularly when different substances are in the sample wells. Instead, it may be desirable to just draw the substances from the sample wells, across the surfaces sealed by the orifices, and into the common pump wells 622 and 624. Therefore, wells 622 and 624 would also serve as the collective drains for the sample wells.

Similarly, with regards to the 96 well spotter embodiment, if a column of wells are dedicated as pump wells then, the spotter would have 88 orifices. If a row was dedicated as pump wells then, there would be 84 orifices. Similarly, a 384 well spotter could have 368 or 360 orifices. A 1536 well spotter could have 1504 or 1488 orifices. However, any number of wells, in any location on the spotter, may serve as sample wells and pump wells.

Pumping may be accomplished by a variety of devices as will be understood by one of skill in the art. Additionally, any number of pumping mediums may be used for delivering positive and vacuum pressure to the samples. In the examples discussed below air is used; however, any fluid may be used.

Figure 13:
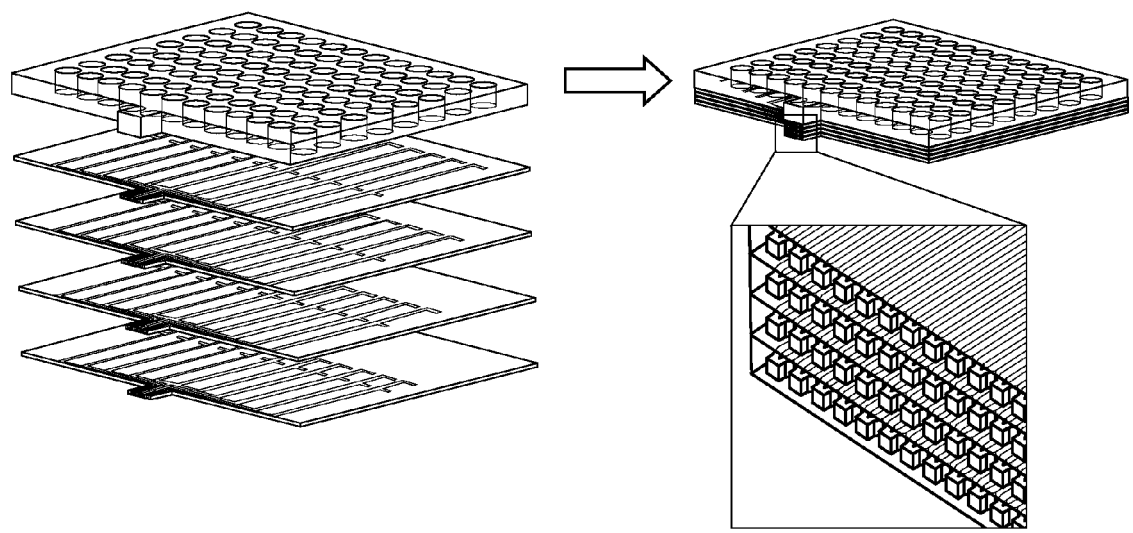
FIG. 13 is an embodiment of a 48-orifice spotter.

As illustrated in FIG. 13, the microconduits may be of varying lengths. When the same pressure is applied to microconduits of the same diameter, containing the same substance, but of different lengths, different substance flow rates result. The microconduits may be modified to create a uniform flow rate between microconduits of different lengths. The pump may be varied as is known in the art to vary the flow rate of a substance. Additionally, the microconduits and orifices may be modified to vary the flow rate of a substance. The wells may also be sized to hold a specific quantity of a substance.

Figure 3:
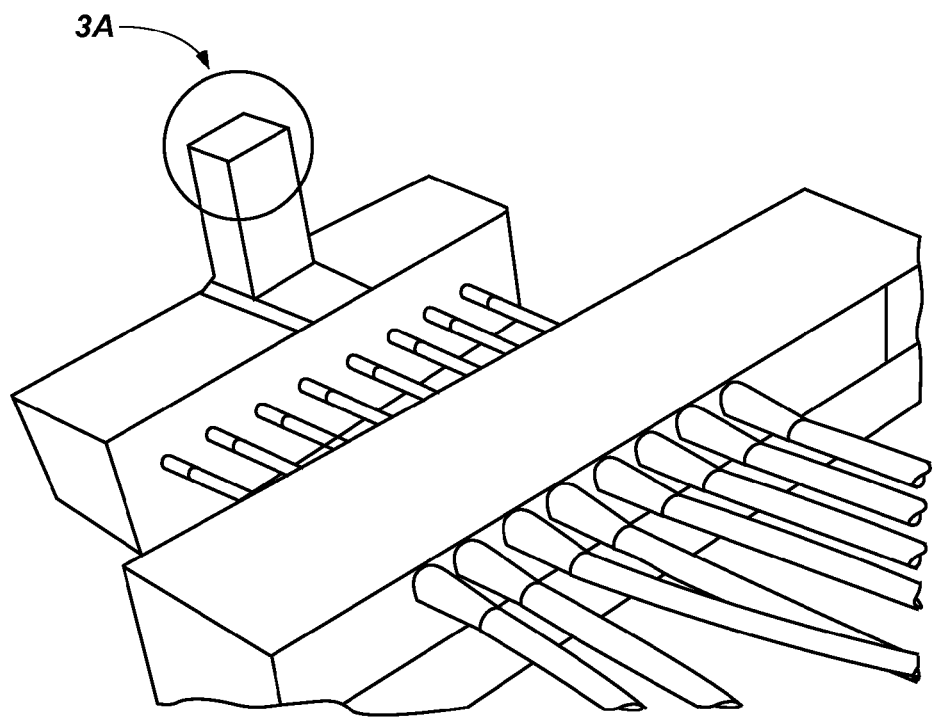
FIG. 3 is one embodiment of a four-orifice spotter.
Figure 3A:
FIG. 3A is a close-up of the orifices.

FIG. 3A and the inset in FIG. 13 illustrate one embodiment of an orifice and an accompanying microconduit junction at the orifice. FIG. 3A and the inset in FIG. 13 may also be described as illustrating apertures within microconduits. These FIGS. illustrate a rectangular orifice. However, the orifice may be any number of geometries. Also, any number of structures may be incorporated within the microconduit junction near the orifice.

Additionally, more than one sample well may be connected to an orifice. Also, sensing components may be integrated into the spotter for sensing at the spotter face. A few examples of sensing components are wave guides and thermocouples among others. However, the sensing components could be built into the surface against which the spotter orifices seal as well.

The spotter in the examples below was fabricated from polydimethylsiloxane (PDMS); however, the spotter may be fabricated out of any suitable material that is compatible with the substances to be flowed through the spotter. Examples of compatible materials include, but are not limited to: silicon; silica; PDMS; gallium arsenide; glass; ceramics; quartz; polymers such as neoprene, Teflon™, polyethylene elastomers, polybutadiene/SBR, nitrites, nylon; metals, and combinations thereof. It may be desirable to build the spotter out of material for which the substances to be flowed (e.g., a solute) have a low affinity for, thus, reducing binding of the substance within the spotter microconduits. Additionally, the inner diameter of the microconduits may be coated with suitable material to reduce the affinity between the substances being flowed and the microconduits themselves.

The spotter may be loaded and unloaded by well plate handling equipment. A well plate handling device may include both positioning equipment as well as sample loading equipment. A robot could be constructed that both loaded the spotter, used the spotter to fashion an array, tested the array, and then unloaded any remaining substances in the spotter. Of course, these functions could be carried out by individual devices working in conjunction with the spotter. Additionally, it is possible to integrate the loading and unloading of the spotter as well as its actual use into a PC. A Graphic User Interface (GUI) program may be developed for manipulating the devices using and working with the spotter. Automated as the term is used herein encompasses manipulating the spotter via robots as well as interfacing the spotter with a pump such as shown in FIG. 7.

FIG. 13 illustrates one embodiment of making a spotter. Spotter layers containing microconduits are produced by molding a silicone polymer onto micro fabricated molds. Alternatively, microconduits could be etched into thin layers of an appropriate material. As many layers as necessary may be stacked together. FIG. 13 illustrates the ease with which the spotter may be scaled to include hundreds or thousands of orifices and microconduits. A top layer containing the wells is added to the stack. Numerous fabrication techniques are known in the art.

Figure 21:
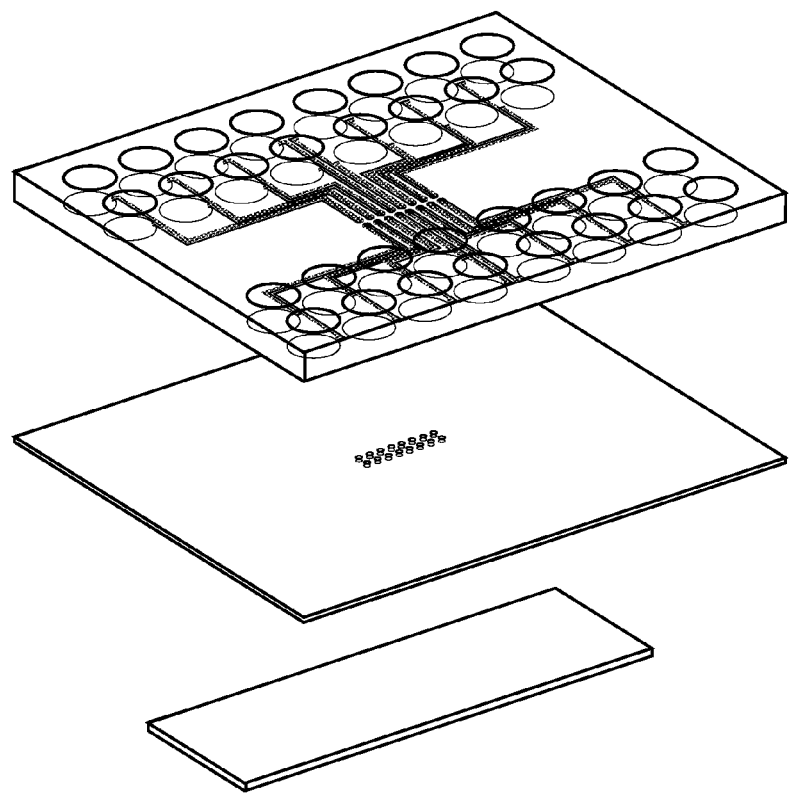
FIG. 21 is an illustration of one embodiment of a 16-orifice spotter.
Figure 22:
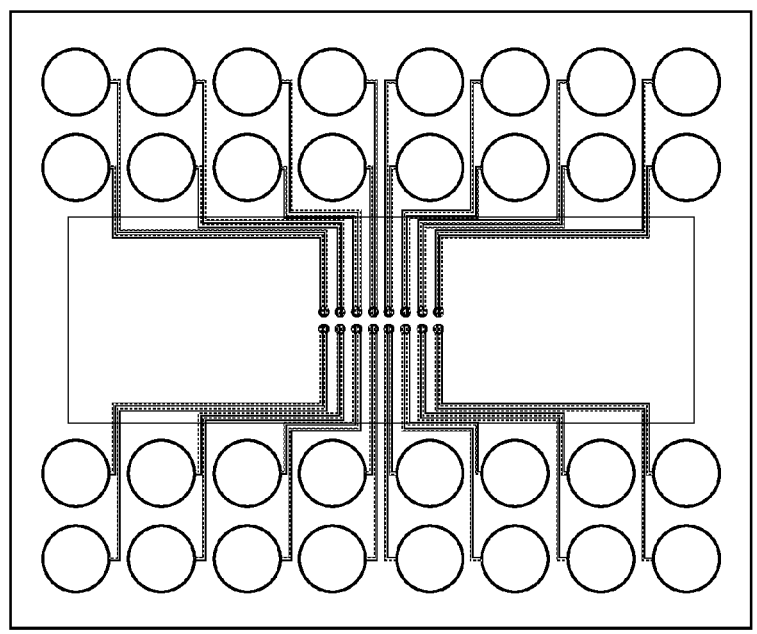
FIG. 22 is a plan-view of FIG. 21.

FIG. 21 illustrates another embodiment of making a spotter. A first layer may contain holes which will serve as the wells. A second layer contains the channels. And third layer contains the orifices that will eventually seal with a surface to be spotted. FIG. 21 shows the first second layers as one layer. FIG. 21 also shows a microslide a completed spotter could be sealed against. FIG. 22 illustrates a top view of FIG. 21. The different layers may be formed and combined by numerous methods known in the art.

Figure 20:
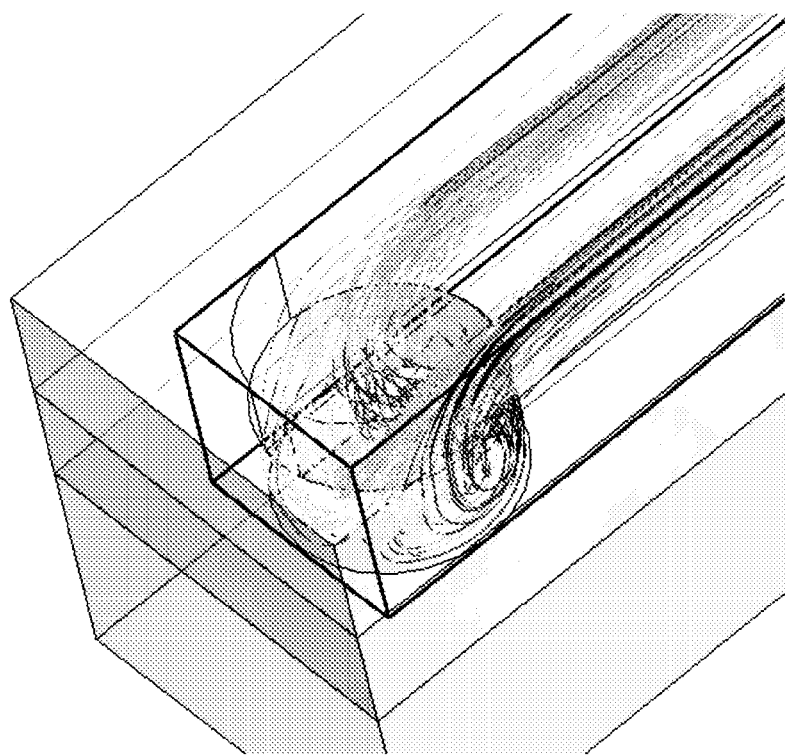
FIG. 20 is an illustration of one embodiment of a spotter.

FIG. 21 also illustrates one embodiment of orientating the spotter face along the bottom of the spotter. The wells are located along the top surface of the spotter. Microconduits would still connect two wells to a single orifice. FIG. 20 illustrates a potential 3-D fluid flow velocity profile at the junction between two microconduits and an orifice. A substance would essentially dump from one microconduit into an orifice where the substance contacts the spot area and then flow back up into the second microconduit. Each of the microconduits shown in FIG. 20 would also be connected to a separate well. This embodiment may still be viewed as a single microconduit or fluid pathway with a hole in the sidewall where each end of the microconduit is connected to a well.

FIG. 21 illustrates an embodiment with 32 wells, 32 microconduits, and 16 orifices. Also, as discussed above, FIG. 21 could be altered to have 28 orifices. 28 orifices would serve as sample wells and 4 wells as pump/drain wells in a similar manner as discussed above with reference to the 16-well spotter.

The bottom surface of the FIG. 21 spotter would then be pressed against a surface to form a seal with the surface. The bottom surface could be easily patterned to mate with an uneven surface.

Given the availability of inexpensive materials and the possibility for high volume manufacturing, even disposable spotters may be manufactured. 2.0 Uses One embodiment of the invention is a method of depositing at least one substance on a surface including loading a multiplicity of storage zones of a microspotter, via sample handling equipment, with the at least one substance; placing a face of the microspotter in proximity to the surface sufficient to form a seal between the microspotter face and the surface, wherein the microspotter face includes orifices fluidicly connected to the multiplicity of storage zones; flowing the at least one substance from the loaded multiplicity of storage zones to the orifices and into contact with the surface sufficient to deposit at least a portion of the at least one substance on the surface; and flowing the remaining undeposited at least one substance to a previously unloaded multiplicity of storage zones.

Another embodiment of the invention is a method of loading a spotter for depositing a substance on a surface including positioning a spotter via a positioning means; and loading the substance into a plurality of wells of the spotter via a loading means, the spotter comprising a means for holding a plurality of wells, the wells having a predetermined spacing between adjacent wells, a plurality of microconduit means connected to each well, and aperture means within said plurality of micro conduits, the aperture means arranged operable to form a seal with the surface.

The spotter may be used to sequentially flow different substances through the microconduits. Therefore, the spotter may be used to perform surface modifications, deposit biomolecules, carry out wash steps, and deliver reagents for chemical reactions. During these different steps, each spot is kept isolated from the other spots and the atmosphere.

The spotter may be used to deposit highly concentrated spots of chemically- or biologically-sensitive materials on a microarray substrate. It can also be used to perform various chemistry steps on the same spots, or selectively remove biomolecules from microscale sections of a surface for off-surface analysis. The spotter may be used to fabricate protein microarrays, but any molecule that is compatible with the flow system of the spotter can be used. The Spotter may be used to handle standard Biacore immobilization chemistries on, for example, a FLEXchip on a massively parallel scale.

Also, a typical ELISA could be completed using only the spotter. An antibody to be captured could be flowed through the microconduits and deposited on an appropriate surface. The antibody could then be washed and interrogated.

In terms of sensing methods using the spotter, the modes are hugely varied, but some of the biochemical uses are:

Surface plasmon resonance (SPR)-spotted recognition molecules such as antibody proteins can spotted in various patterns to create a high-throughput biomolecule assay system using an SPR substrate. The spotter could be used to deposit the capture materials followed by the sample. Readout of binding would be made at each point of the array using SPR instrumentation.

Optical-multiple high-concentrate dye spots can be applied in an array format on a surface to act as a multiple-analyte chemical-specific sensor with an increased signal-to-noise ratio, or materials such as cells can be deposited, tested, and labeled using the spotter for fluorescence/absorbance/reflectance detection. The latter application bears great significance to the field of drug discovery, by allowing multiple types of cells to be tested simultaneously with varying chemicals. DNA hybridization, is also compatible with the spotter, both for oligonucleotide deposition and labeled-sample interaction.

Quartz crystal microbalance (QCM)-antibody-antigen interaction is the most significant application of QCM systems, although any surface-target molecule can be detected by QCM. The spotter could be used to address multiple QCM sites simultaneously.

The spotter can fabricate high-quality sensing spots, and deliver target compounds to that specific spot in a controlled and predictable manner, while keeping the spot isolated from the rest of the spots in the array. The relative low cost of the spotter allows the spotter to be used in both full-scale commercial applications, as well as small research environments for production of custom sensor arrays. These arrays can be used in either a military application, laboratory, medical research and diagnostics, or point-of-care setting, for rapid parallel detection of various analytes on a larger scale.

The continuous flow nature of the spotter allows not only higher quantity deposition at the spot area to be performed, but also allows multiple layers of biomolecules to be deposited, facilitating sensing on the spots. Just a few examples of the substances that may be deposited by the spotter are DNA, RNA, proteins, sugars, lipids, cells, and related chemicals. Thus, one device can do the spotting, assay, and analysis, eliminating multiple pieces of equipment, speeding assays significantly, and improving hybridization conditions. A continuous sensing system is possible where a continuous flow of a substance of interest could be passed through the channels and continuously monitored. The continuous flow capable with the spotter is able to speed hybridization, washing, and analyte capture, meaning that a typically ELISA could be reduced from several hours to several minutes. The spotter can be used in a flexible configuration, allowing various sizes of arrays manufactured with the spotter on the same surface.

The spotter may be integrated with numerous microfluidic systems. A few examples are: ink jet printers, mass spectrometry systems, spotting robots, and sample injection systems.

The sample size of substances can be very small. Tests have been performed in some embodiments with as few as 10 micro Liters. Additionally, smaller initial substance sample sizes can be used by diluting the substance to take advantage of the concentrating effects of the flow deposition. The dead volume of the microconduit loops from well-to-well for some of the embodiments ranges from 10 to 30 nanoLiters.

A few examples of surfaces that may be used for depositing substances with the spotter include: glass, silicon, streptavidin-gold chips, plain gold FLEXchips, dextran-coated FLEXchips, and any number of surfaces.

EXAMPLES

Deposition of Protein A on a streptavidin gold chip surface was attempted with a single orifice spotter. Deposition of Protein A on a plain gold FLEXchip surface with a four orifice, an eight orifice, and a 48 orifice embodiments. The tests show that Protein A can be immobilized on a streptavidin gold chip and on a plain gold FLEXchip surface via flow deposition through the spotter. Significant variability between the spots occurred in each of the experiments. This was likely due to differences in the flow rates between the microconduits.

Example 1

Single Orifice Spotter

Deposition of Protein A was attempted with a single orifice spotter similar to that shown in FIG. 3, to validate the design concept displayed in FIG. 1. Protein A (ImmunoPure Protein A, cat #21181, Pierce Inc.) was biotinylated with Biotin (EZ-Link Sulfo-NHS-Biotin, cat #21217, Pierce Inc.) to provide specific adhesion to a surface plasmon resonance (SPR) streptavidin gold chip (8500 streptavidin affinity chip, part #4346388, AB). The protein solution was diluted to a concentration of 0.15 [mu]g/mL in 0.1*PBS buffer (0.19 mM NaH2PO4, 0.81 mM Na2HPO4, pH 7.4 and 15 mM NaCl) and supplemented with 100 [mu]g/mL BSA to prevent non-specific adhesion. To recirculate the solution over the chip surface, 200 [mu]L of protein A solution was loaded into a Phynexus MicroExtractor 100 syringe pump and flowed continuously back and forth through the spotter at 75 [mu]L/min for 1 hour. A wash step was then performed using 800 [mu]L of 0.1*PBS with 100 [mu]g/mL BSA. At the end, the sample was removed from the surface by withdrawing air through the assembly, and the chip was then washed using water.

Figure 2:
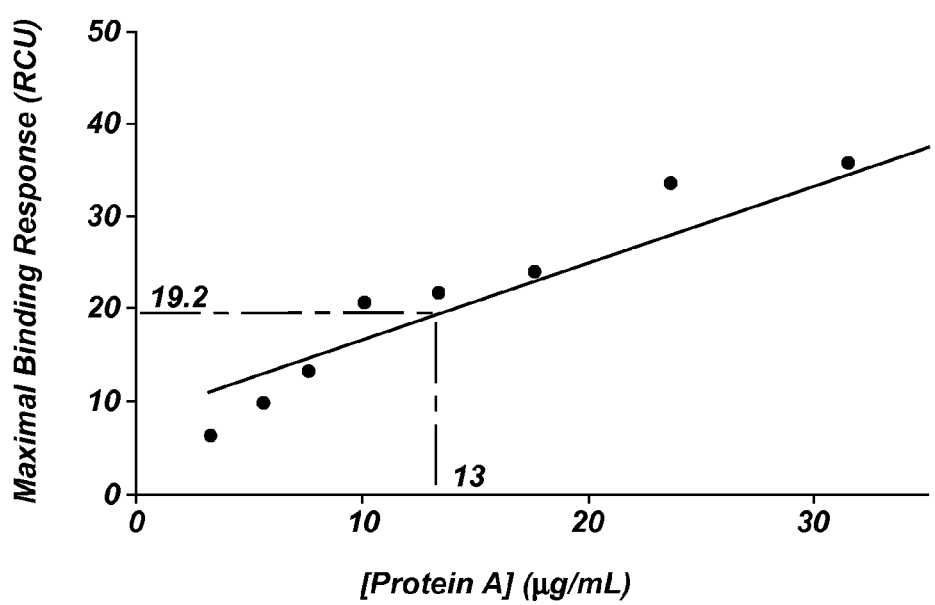
FIG. 2 is a calibration curve to compare spot deposition concentration yielded by one embodiment of the invention with the spot deposition concentration of a pin spotter.

To compare the spotter immobilization to conventional methods, protein A was also immobilized using solid-pin spotting with a Genetix Q array Mini spotter. Increasing protein concentrations were deposited to create a calibration curve of SPR response to deposited concentrations of protein A. This curve was used to calculate an equivalent concentration for use of the spotter, to determine the factor increase in deposition density. The horizontal line extending from the y-axis to the calibration curve shown in FIG. 2 represents the maximal signal from the spotter of 19.256 response change units (RCU). Based on the standard curve this signal would correspond to 13 [mu]g/mL of pin-spotted protein A. Since the concentration of protein A immobilized using the spotter was only 0.15 [mu]g/mL, immobilization via the spotter yielded an 86-fold increase in sensitivity versus solid pin-spotting.

Example 2

Four Orifice Spotter

An embodiment of a four orifice spotter is shown in FIGS. 3 & 3A. ImmunoPure Protein A (Pierce, cat #21181) was prepared in PBS buffer (20 mM NaH2PO4/Na2HPO4 pH 7.4, 150 mM NaCl) at a concentration of 5 mg/mL. The ports that address each spot were connected together using tubing so the same sample was flowed across the four spots. The spotter was mounted over a FLEXchip plain gold surface and the sample was flowed over all four spots manually using a syringe for approximately 1 hour. At the end, the spots were washed using PBS buffer and the chip was mounted according to the instructions of the manufacturer.

Figures 4A, 4B:
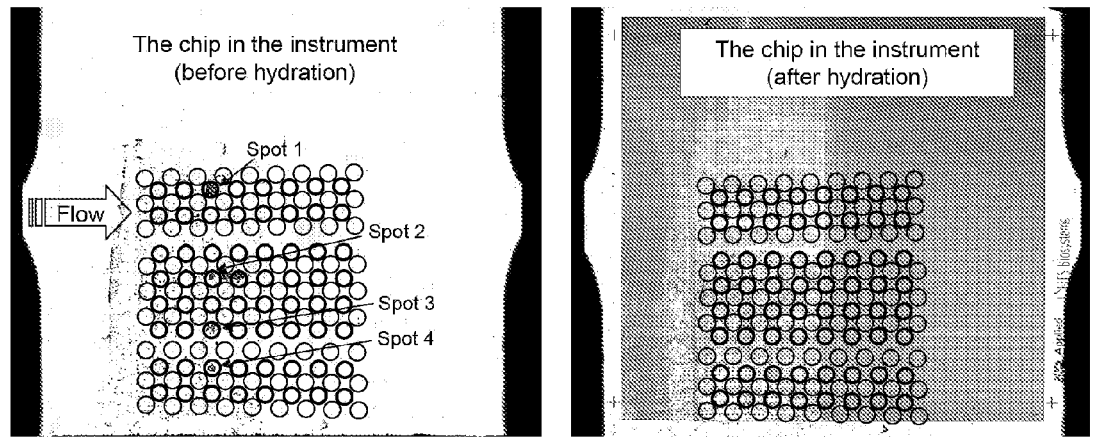
FIG. 4A illustrates a surface with spots deposited with the embodiment of FIG. 3.
FIG. 4B is the same surface shown in FIG. 4A after hydration of the surface.

The protein A-adsorbed chip was inserted in the FLEXchip array instrument. The four areas where protein A was deposited were visible, so the spots could be assigned where the immobilized material is located. An example of the assigned spots is shown in FIG. 4A; the four spots labeled 1-4 correspond to immobilized protein A spots, while the remaining spots are used for monitoring of the binding signal of IgG over protein A. For this experiment all spots will be treated the same because we are interested in observing the distribution of binding signal on the array based on the spotting pattern. Spots 1-4 correspond to the orifices shown in FIG. 3A.

After the assignment of the spots, the gold chip was blocked using 5 mg/mL BSA. A picture of the chip after hydration is shown in FIG. 4B. The binding assay was performed at 25 [deg.] C. in PBS buffer supplemented with 0.2 mg/mL BSA. The buffer signal was monitored for five minutes at a flow rate of 0.5 mL/min to establish a stable baseline. Human IgG1, [kappa] (Sigma cat #15154) was prepared in buffer at 100 nM and injected over the Protein A surface at 0.5 mL/min for 6 minutes. Buffer was then flowed for an additional 10 minutes to monitor the dissociation phase of the complex.

Figure 5:
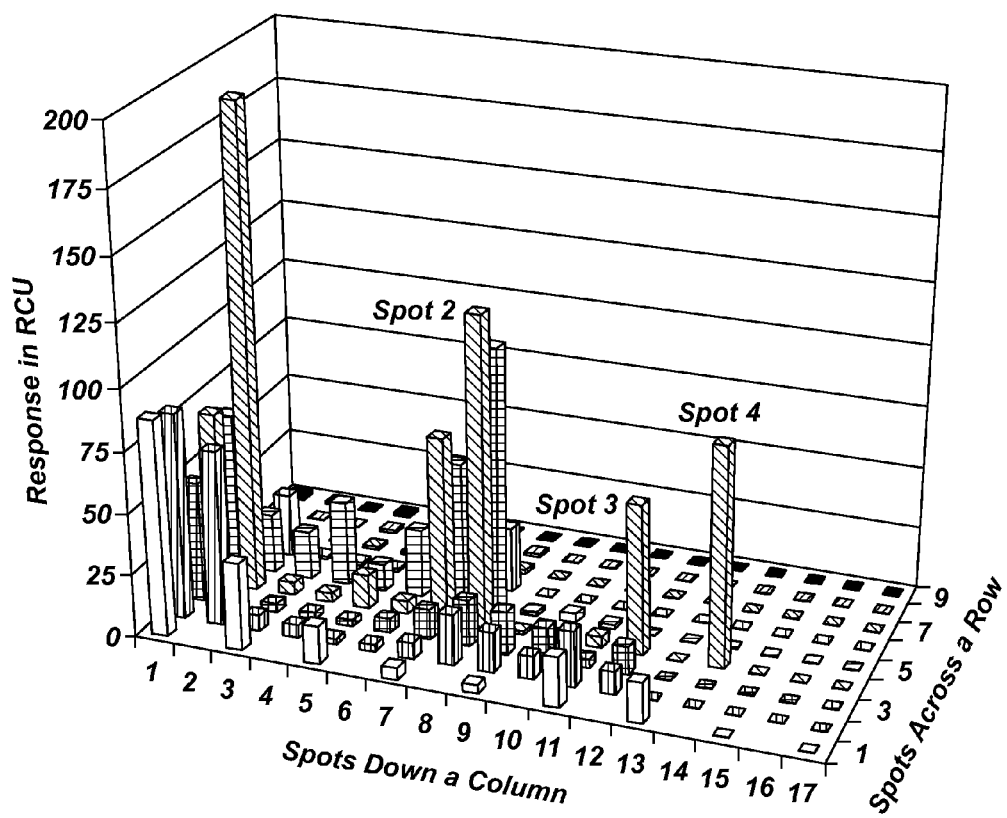
FIG. 5 is graphical illustration of the data determined from FIGS. 4A and 4B.

IgG bound to all the protein A spots, indicating that protein A adsorbed efficiently to the gold surface under the conditions tested. Spot 1, which was the first spot deposited during the spotting protocol, resulted in the highest binding signal, see FIG. 5, approximately 195 response change units (RCU). In this region there was leakage to the surrounding spots, as observed by the high binding signals in the binding panel of spot 1. From FIG. 4A, spot 2 appears to cover two spots, which agrees with the observations of the binding experiment shown in FIG. 5. Binding was detected over the two neighboring spots at 120 and 105 RCU. Binding responses were also detected in the spots exactly above the protein A-immobilized spots. Similar to spot 1, binding signals over the spots located down the row from the protein A spot were not detected. The signals over spots 3 and 4 appear much cleaner than the signals of spots 1 and 2 with minimal binding responses over the surrounding spots. This is likely due to a misalignment when the orifice was placed against the surface, leading to poor sealing in spots 1 and 2. Moreover, microscopic grooves were detected on the sealing face due to the method of cutting the spotter face with a razor blade (see FIG. 3). Alternative ways of cutting the spotting face to produce a more planar surface will likely produce a more effective seal.

Overall, the results of this experiment were very encouraging, showing that Protein A could be efficiently immobilized over the surface of a gold chip to detect binding of human IgG.

Example 3

Eight Orifice Spotter

In Examples 1 and 2, external fluidic connections were made by inserting a 20-gauge needle into the microconduits of the spotters and making connections to the needle (See FIG. 3). This technique proved to be robust and sufficient for small scale research devices. However, scaling of the device would quickly become problematic. Furthermore, a method was necessary that would allow simplified loading of samples. The solution, shown in FIG. 6, was to place sample wells directly above the microconduits. To simplify substance transfer, the wells were placed in the same spacing and format as those of a 16 well plate. This allows researchers to use current sample handling equipment to load and unload the device.

Another significant challenge to parallel fluid delivery was the pumping of the fluids. In Examples 1 and 2, pumping was accomplished by connecting a syringe pump or vacuum line to each individual outlet line. In the embodiment shown in FIG. 6, it is possible to pump all the channels at once. Each flow loop is connected to two wells, one for sample loading and one for pumping interface. A simple manifold is placed over the first line of wells and a pump is used to deliver alternating vacuum and positive pressure, cycling the solutions back and forth between the two connected wells.

Example 3

Summary

Binding of IgG to the protein A spots was detected in seven out of the eight spots deposited on the gold chip (See FIGS. 9-12). Unlike what we detected with Example 2, binding responses above the baseline were not detectable over the spots in the front of protein A spots suggesting that the spotting is specific over the allocated regions. Signal was detected over the spots following the spotted protein A spots though this is not related to the spotting process but spreading of the samples at high concentrations of protein used for spotting. The IgG binding signals ranged form 100-180 RCU, indicating that there is variability among the amount of protein A deposited over each spot. These results demonstrate that the spotter can be effective in immobilizing ligands to the chip surface yet, this spotter can be further improved to generate more uniform spots.

Example 3

Test Methods and Results

Figure 8:
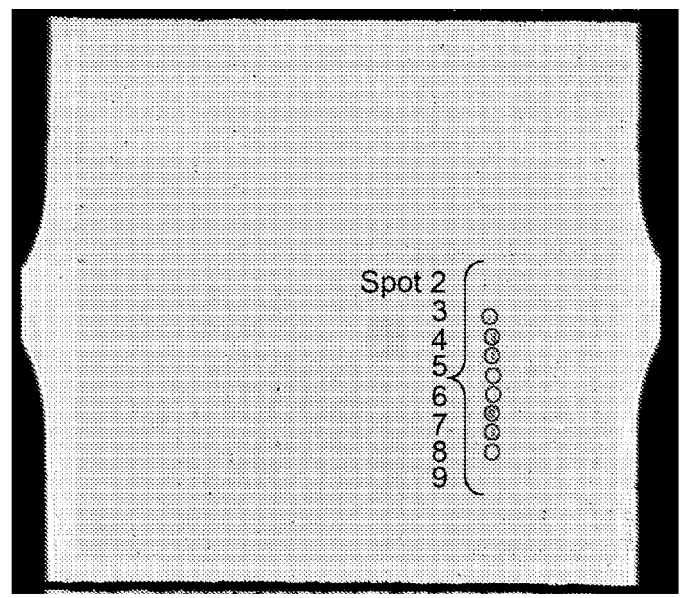
FIG. 8 illustrates a surface with spots deposited with the embodiment of FIG. 6.

The same sample of protein A that was used in Example 2 was also used for this assay [ImmunoPure Protein A (Pierce, cat #21181) at 5 mg·mL in PBS buffer (20 mM NaH2PO4/Na2HPO4 pH 7.4, 150 mM NaCl)]. The spotting was performed over a plain gold FLEXchip and the protein A was flowed over the chip for approximately 1 hour. At the end the spots were washed using PBS buffer and dried. The resulting spots are shown FIG. 8.

Seven of the eight protein A spots were visible after the chip was inserted into the FLEXchip array instrument. The spots were 200 microns square, roughly half the size of the spots deposited over with the four orifice spotter. A grid of 10*10 spots was assigned to enclose the eight protein A spots and the surrounding area (although the spotting pattern is a 10*10 grid, inclusion of the reference spots results in a grid of 21*11, as shown in the histogram). For reference, the protein A spots are located over the seventh column, spots 2-9. An empty spot was assigned at the top and the bottom of the column to control for contamination of the protein A sample to the surrounding area.

The binding experiment was performed under conditions similar to Example 2. The gold chip was blocked using 5 mg/mL BSA and the assay was performed at 25[deg.] C. in PBS/0.2 mg/mL BSA buffer. The buffer signal was monitored for five minutes at a flow rate of 0.5 mL/min to establish a stable baseline. Human IgG1, [kappa] (Sigma cat #15154) at 100 nM was flowed over the protein A surface at 0.5 mL/min for 6 minutes. Buffer was then flowed for an additional 10 minutes to monitor the dissociation phase of the complex.

Figure 9:
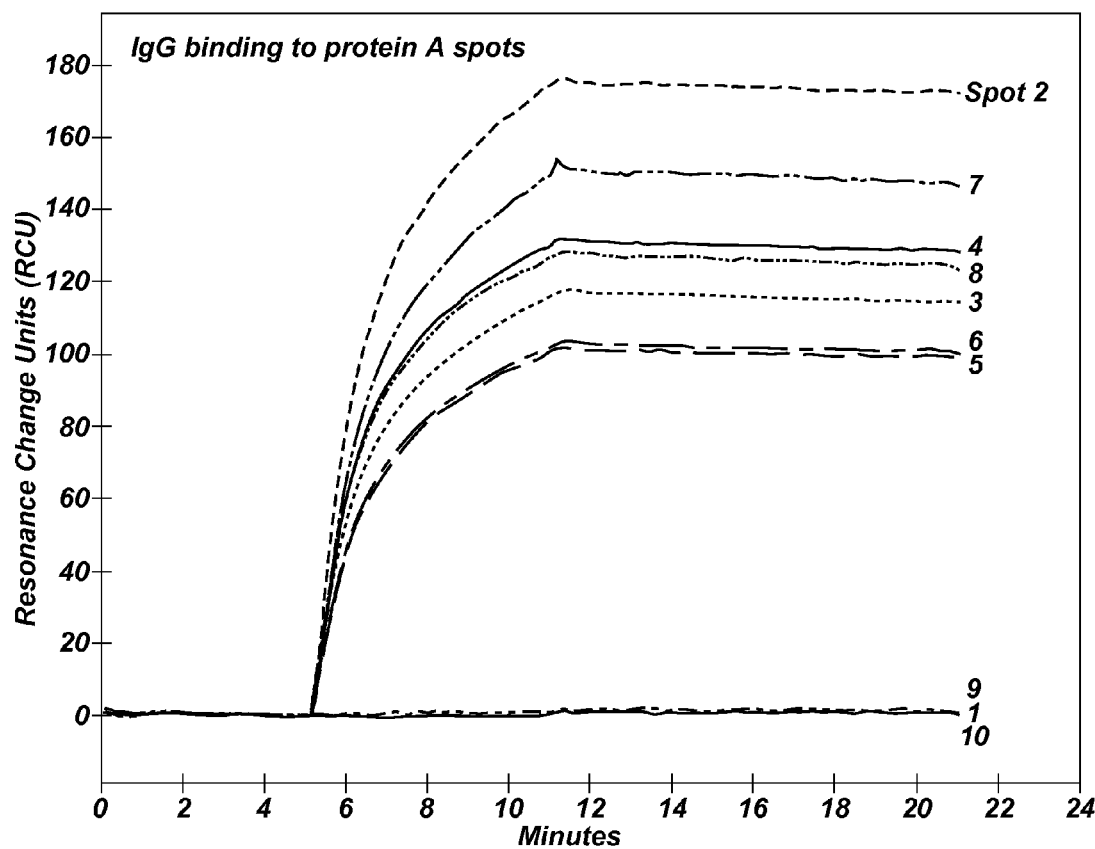
FIG. 9 is a graph of data based upon FIG. 8.
Figure 10:
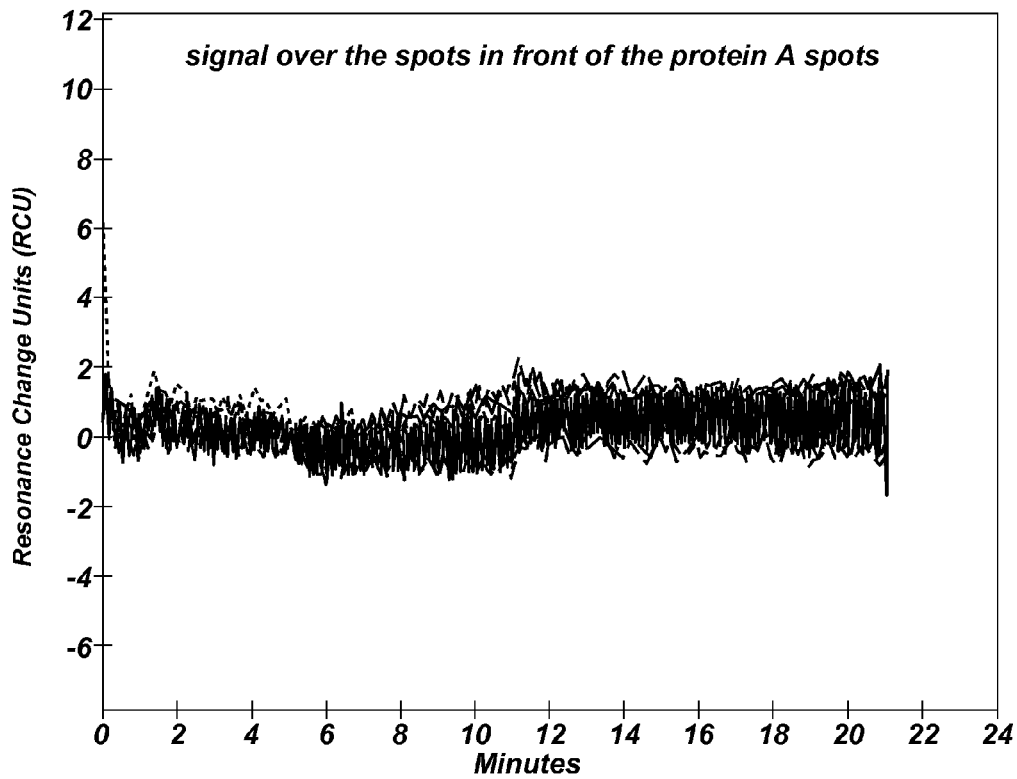
FIG. 10 is a graph of data based upon FIG. 8.

IgG binding was detected over seven of the eight spots, as shown in FIG. 9. Spot 9 did not show any binding signal suggesting that the microchannel may have been clogged. For the remaining spots, the binding signals ranged from 100 to 180 RCU. Ideally, the responses of these spots should be more uniform with each other since the same material was circulated back and forth at the same rate. The differences are likely due to varying flow rates between the channels. As seen in FIG. 6, the channels lengths vary due to the sample handling format. Because all the channels of this device had equal cross-sectional dimensions, the shorter channels experienced faster flow rates. Other embodiments may be designed to address this issue.

Figure 11:
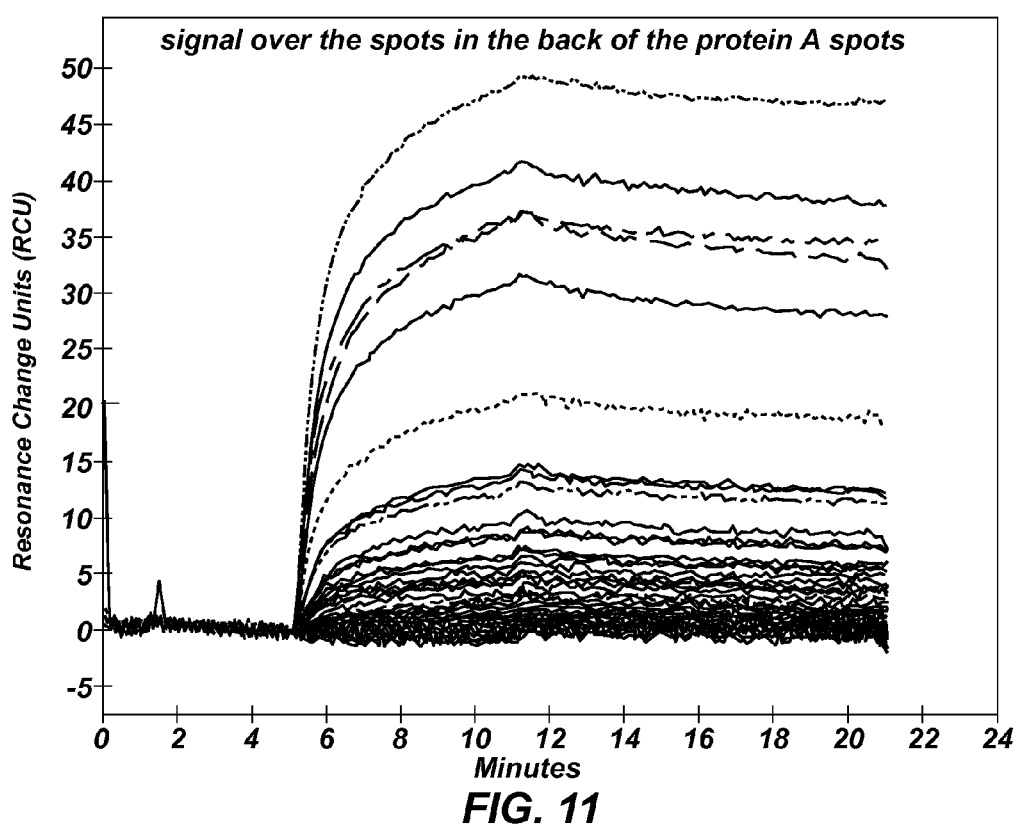
FIG. 11 is a graph of data based upon FIG. 8.
Figure 12:
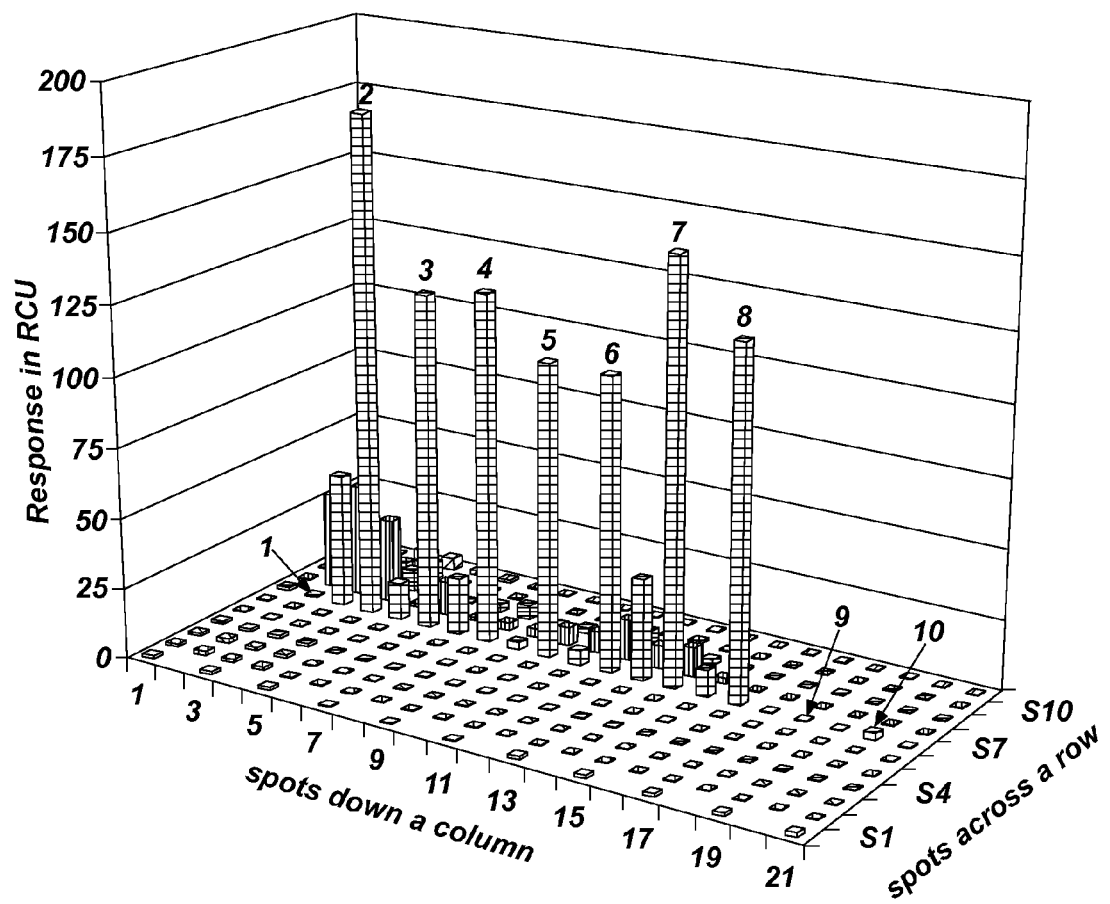
FIG. 12 is a graph of data based upon FIG. 8.

The leakage problems encountered with the four orifice spotter have been greatly improved in this instrument. FIGS. 11 and 12 show the signals detected over the areas in the front and the back of the protein A spots. The left-hand panel shows an overlay of all the signals from the first six columns. Sample leakage was not detected this time, since the signals from all spots overlay at the baseline. Unlike the signal in the front of the protein A spots, spots in the back of the protein A spots (columns 8-11) showed a range of binding responses from 0-50 RCU, suggesting that the back spots are contaminated with protein A. This is not associated with the spotting but rather with the high concentrations of protein (5 mg/mL) used in this assay. Because of such high protein concentrations, it is likely that some of the protein fails to covalently adsorb to the gold surface but instead remains aggregated over the gold chip. As a result when the chip is filled with buffer, the protein flows over the spots following the protein A spots.

The distribution of the binding signals as shown in the histogram (FIG. 12) shows that the contamination is more prominent closer to spots that showed high binding signals, for example spot 2. Spots 5 and 6, which showed low binding responses, showed responses of >5 RCU. Once we have developed an optimized spotting protocol we plan to use proteins of much lower concentrations for spotting which would minimize this effect.

In conclusion, the experiment was successful in terms of showing that the automated eight orifice spotter can deposit eight spots simultaneously. Although this device shows many improvements over the manual four orifice spotter, the spot uniformity will need to be further improved. In addition, increasing size of the spots slightly will allow signals to be detected using protein samples of lower concentrations.

Example 4

48 Orifice Spotter

Testing of an embodiment of a 48 orifice spotter. In this example, the 48 orifice spotter addresses a two dimensional 12*4 array, as shown in FIG. 13. The device was designed to integrate with a 96 well plate for simplicity in substance handling. Each channel loop system is connected to two wells-one for sample substance loading and one for pumping, which is accomplished by applying alternating vacuum and positive pressure. In this embodiment, the lower block of 48 wells is covered by an air manifold and samples are loaded into the upper block of 48 wells.

FIGS. 14 and 15 show an assembled 48 spot device. Spot sizes are 400 microns by 200 microns. Spot pitch within rows is 400 microns. Spot pitch from row to row is approximately 1.5 mm, though some variability exists (FIG. 15). This was due to the use of open molds and irregularities in the levelness of the curing oven. In the future, spotters may be manufactured with closed injection molds, among other techniques, allowing a precise control of layer thicknesses and therefore of spot pitch.

Example 4

Preliminary Tests Results

Figure 16:
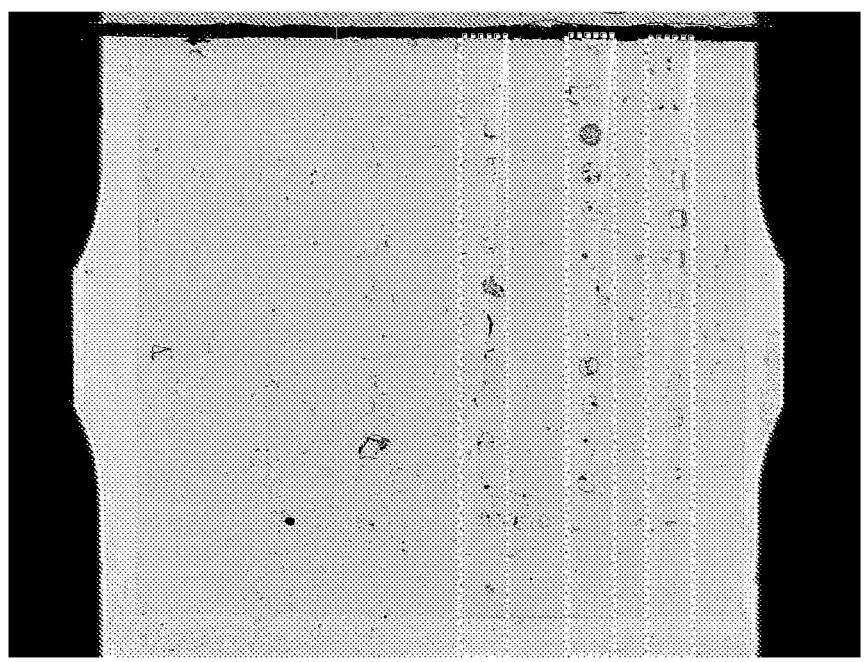
FIG. 16 illustrates a surface with spots deposited with the embodiment of FIG. 14.

A dilute solution of Protein A (in PBS at 0.4 mg/mL) was immobilized over a plain gold chip for approximately 30 minutes. An image of the printed chip is shown in FIG. 16. The spots were printed in a 4*12 format. When the chip was inserted in the FLEXchip platform most of the spots in three columns were visible. The device may have been misaligned on the FLEXchip during printing. By comparing FIGS. 15 and 16, it appears that the left most column in FIG. 16 corresponds with the bottom row of spots in FIG. 15, due to the slight spacing irregularities between rows 3 and 4. Therefore, one row of spots was likely deposited outside of the active chip area and the following results examine 36 spots arrayed in a 3*12 configuration.

Figure 17:
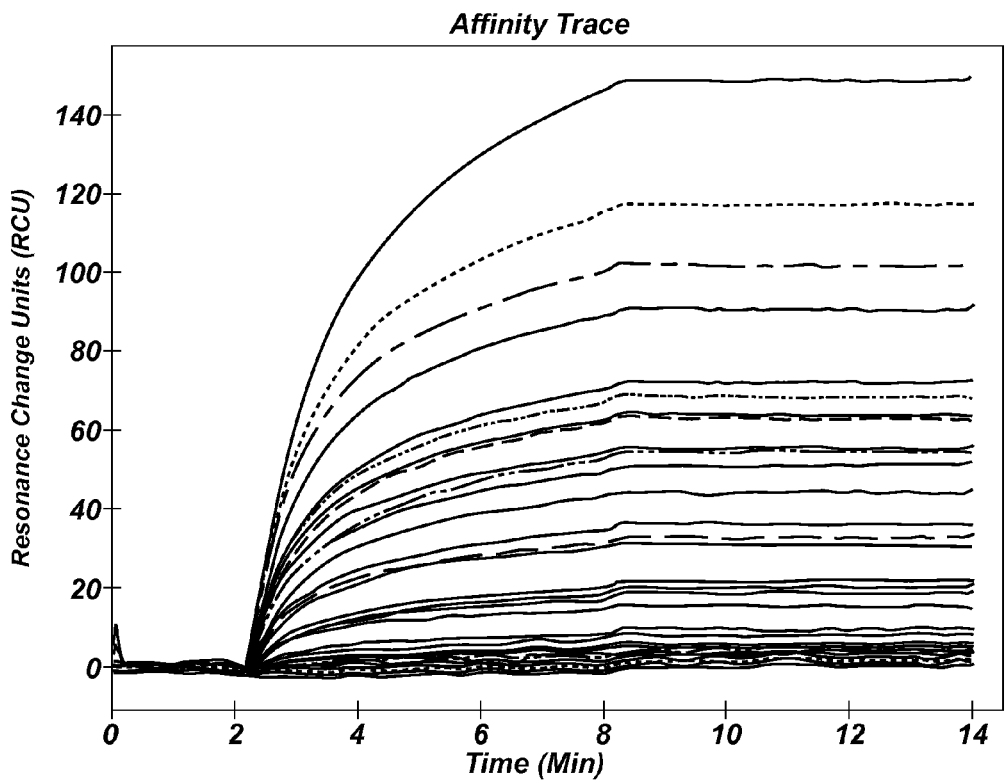
FIG. 17 is a graph of data based upon FIG. 16.
Figure 18:
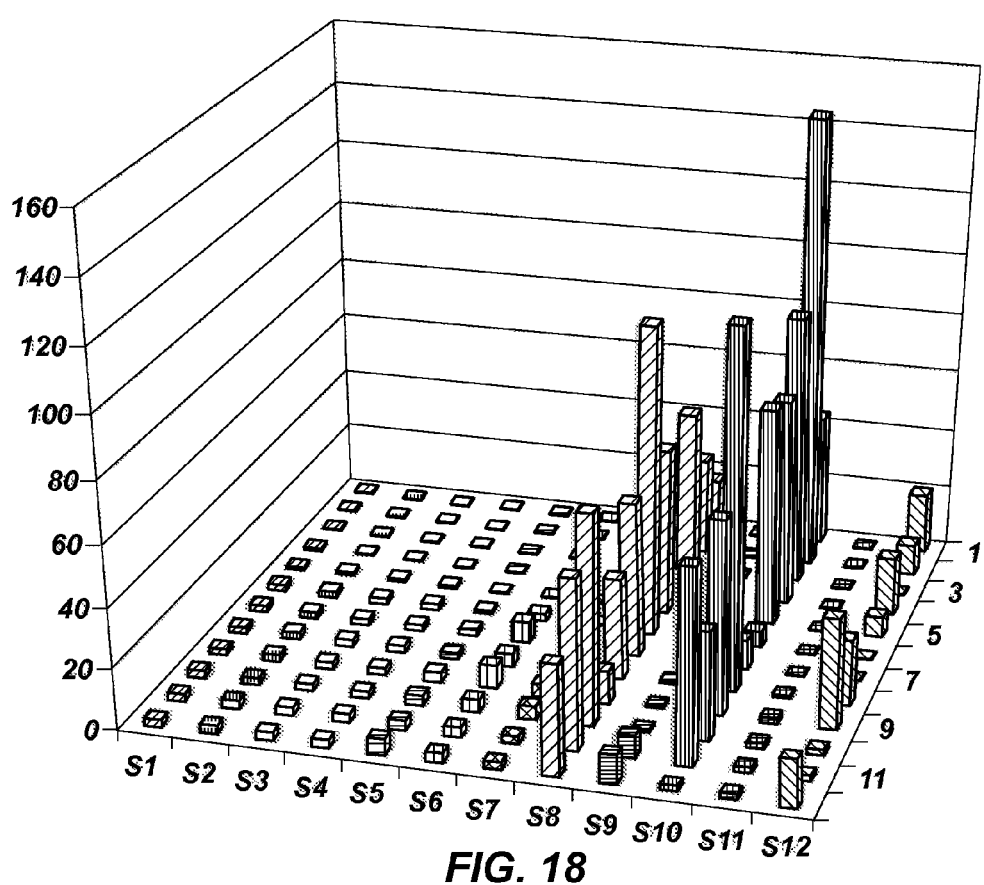
FIG. 18 is a graph of data based upon FIG. 16.

Human IgG was prepared in running buffer (PBS, 0.2 mg/mL BSA) and tested for binding at 100 nM. The association phase was monitored for 6 minutes at a flow rate of 500 [mu]L/min. The binding profile for the spots are shown in FIGS. 17 and 18. Although most spots produced binding signals, there was variability among the responses. FIG. 18 shows the distribution of the responses. Responses in the columns S6, S8, and S10 correspond to protein A deposited. The data show that there is minimal contamination to the surrounding spots since columns S7, S9, and S11 did not show prominent binding responses. This suggests that there is no spreading to the leakage spots. Also, the concentrations of protein A tested are sufficiently low so when the surfaces are exposed to buffer there is no carryover to the spots further along the direction of flow.

The results show that the levels of protein A immobilized were inconsistent among the different spots. Fast flow rates were observed during the spotting (an uncharacterized pump was used), which may have contributed to the variability. In addition, the microconduit design has not been optimized to provide uniform flow between channels.

In conclusion, these results show that a multi-layer device can address a two dimensional array of spots without contamination to surrounding spots. Design changes and pumping modifications could be employed to improve the deposition uniformity between spots.

Example 5

Sandwich Assay

Anti-mouse IgG with biotin (OEM Concepts, cat #G5-MG10-4, 10* diluted) was filled in the wells of a 8-well spotter device. Using a pumping manifold and applying vacuum and pressure alternatively, this was flowed through the microconduits over the surface of a streptavidin coated glass slide (the substrate). The anti-mouse IgG was therefore deposited at specific portions on the glass slide through the orifices in the microconduits. The slide was then blocked with 3% BSA (high purity BSA suspended in PBS) for 10 minutes. Once blocked, it was incubated with mouse IgG diluted in 3% BSA for 5 min. The mouse IgG bound only to the anti-mouse IgG portions of the substrate. After the incubation, the plate washed 3 times with TBST. Then, the substrate was incubated for 5 min with Horse Radish Peroxidase (HRP) labeled goat anti-mouse diluted 1000* in 3% BSA. HRP is a chemiluminescent enzyme used to label antigens and their antibodies to detect their presence. A final wash step was then performed.

Figure 19:
FIG. 19 illustrates a surface with spots deposited with an eight-orifice spotter.

The slide was then examined under a scanner. Only the spots deposited by the spotter should be visible since the HRP attaches only to these portions through the mouse IgG. The 8 spots deposited using the spotter are shown in FIG. 19. This indicated that the spotter can be used for a sandwich assay or an ELISA.

While disclosed with particularity, the foregoing techniques and embodiments are more fully explained and the invention described by the following claims. It is clear to one of ordinary skill in the art that numerous and varied alterations can be made to the foregoing techniques and embodiments without departing from the spirit and scope of the invention. Therefore, the invention is only limited by the claims.

What is claimed is:

1. A method of depositing at least one substance on a surface, the method comprising:
   loading a multiplicity of storage zones of a microspotter, via sample handling equipment, with the at least one substance;
   placing a face of the microspotter in proximity to the surface sufficient to form a seal between the microspotter face and the surface, wherein the microspotter face includes orifices fluidically connected to the multiplicity of storage zones;
   flowing the at least one substance from the loaded multiplicity of storage zones to the orifices and into contact with the surface sufficient to deposit at least a portion of the at least one substance on the surface; and
   flowing the remaining undeposited at least one substance to a previously unloaded multiplicity of storage zones.

2. The method according to claim 1, wherein loading the multiplicity of storage zones comprises loading each of the storage zones with a different substance.

3. The method according to claim 1, further comprising flowing a second at least one substance over the surface without breaking the seal between the microspotter face and the surface.

4. The method according to claim 1, wherein the at least one substance is independently selected from the group consisting of: a protein; a nucleic acid, a cell; a lectin; a synthetic composite macromolecule; functionalized nanostructure; a synthetic polymer; a nucleotides, a nucleoside; an amino acids; a ligand; a chelator; a hapten; a chemical compounds; a sugar; a lipid; a liposome; a tissue sample; a virus; and any combinations thereof.

5. The method according to claim 1, wherein the surface already has a probe on the surface prior to flowing the at least one substance into contact with the surface.

6. The method according to claim 1, wherein the microspotter is integrated in a microfluidic system selected from the group comprising: an ink jet printer system, a mass spectrometry system, a spotting robot system, and a sample injection system.

7. The method according to claim 1, wherein each of the orifices is connected to at least two of the multiplicity of storage zones.

8. The method according to claim 1, wherein the step of flowing the at least one substance from the loaded multiplicity of storage zones to the orifices and into contact with the surface sufficient to deposit at least a portion of the at least one substance on the surface comprises adhering the at least one substance to a surface plasmon resonance chip.

9. The method according to claim 1, wherein the step of flowing the at least one substance from the loaded multiplicity of storage zones to the orifices and into contact with the surface sufficient to deposit at least a portion of the at least one substance on the surface comprises depositing an antibody on the surface, and wherein the method further comprises washing the antibody and interrogating the antibody to perform an enzyme-linked immunosorbent assay.

10. The method according to claim 1, wherein the step of flowing the at least one substance from the loaded multiplicity of storage zones to the orifices and into contact with the surface sufficient to deposit at least a portion of the at least one substance on the surface comprises depositing an antibody on the surface, and wherein the method further comprises applying a chemiluminescent enzyme to the surface so that the chemiluminescent enzyme attaches to the antibody.

11. The method according to claim 1, wherein the step of flowing the at least one substance from the loaded multiplicity of storage zones to the orifices and into contact with the surface sufficient to deposit at least a portion of the at least one substance on the surface comprises depositing cells on the surface, and wherein the method further comprises labelling the cells with fluorescent labels and detecting fluorescence from the cells.

12. The method according to claim 1, wherein the step of flowing the at least one substance from the loaded multiplicity of storage zones to the orifices and into contact with the surface sufficient to deposit at least a portion of the at least one substance on the surface comprises depositing the at least one substance onto a quartz crystal microbalance.

* * * * *